United States Patent [19]

Mast

[11] 4,341,473
[45] Jul. 27, 1982

[54] MEASURING HEAD IN OR FOR A DENSITOMETER

[75] Inventor: Fred Mast, Wil, Switzerland

[73] Assignee: Gretag Aktiengesellschaft, Regensdorf, Switzerland

[21] Appl. No.: 189,115

[22] Filed: Sep. 22, 1980

[30] Foreign Application Priority Data

Sep. 28, 1979 [CH] Switzerland ............... 8791/79

[51] Int. Cl.³ ............................... G01N 21/47
[52] U.S. Cl. ........................ 356/446; 350/314
[58] Field of Search ............... 356/445–448; 350/314

[56] References Cited

U.S. PATENT DOCUMENTS

3,843,235 10/1974 Mino et al. ............... 350/314
4,078,858 3/1978 Mast ........................ 356/446

*Primary Examiner*—Vincent P. McGraw
*Attorney, Agent, or Firm*—Burns, Doane, Swecker & Mathis

[57] ABSTRACT

A measuring head for a densitometer comprises a light source and an optical system for forming a spot of light of defined size on the surface of an object under test. The optical system guides the reflected or transmitted light, depending on the type of densitometer, from the area of the spot to a photoelectric measuring transducer. The light intensity distribution across the spot as seen by the transducer is weighted to have a bell-shaped curve with its maximum at the center of the spot. The weighting may be done in the optical path from the spot area to the transducer or, as described, in the path between the source and spot area by means of a filter comprised of a plano-convex transparent lens and a plano-concave lens of neutral grey glass. The lenses have the same index of refraction and the same curvatures and are joined to form a plane parallel plate having a maximum transmissivity on its axis, the transmissivity decreasing radially from the axis. The head finds particular use for measuring raster-like material such as offset printing.

19 Claims, 4 Drawing Figures

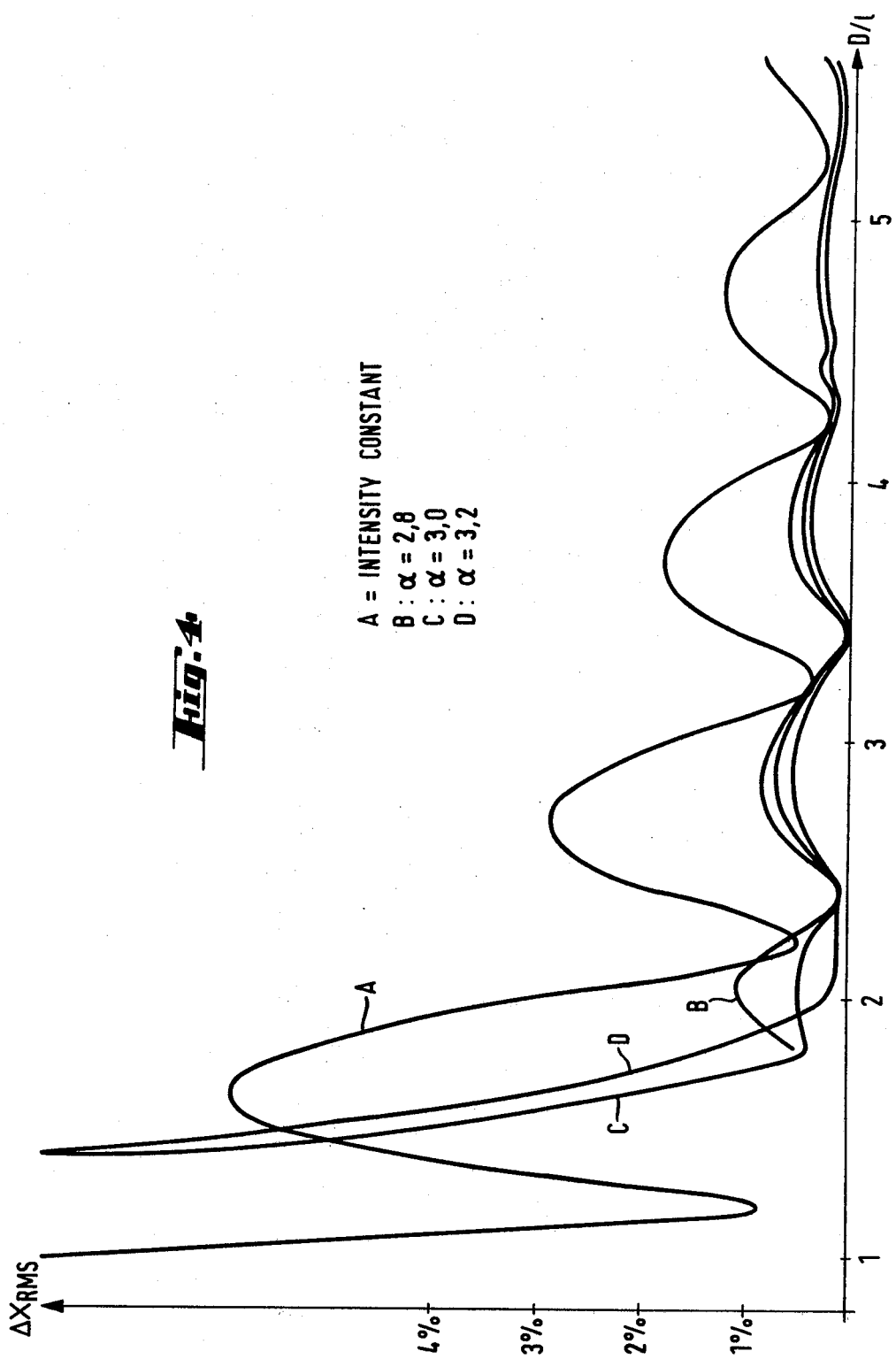

MEASURING HEAD IN OR FOR A DENSITOMETER

FIELD OF THE INVENTION

The invention relates to a measuring head for a densitometer comprising a light source, a photoelectric transducer and an optical system for forming a defined spot of light from the source on the object being measured and for directing light from the spot area on the object to the transducer.

BACKGROUND TO THE INVENTION

It is known that in densitometry, the size of the measured spot, i.e. the area of the measured object which is illuminated by the light source, determines the size of the smallest detectable detail and consequently the resolution. To obtain high resolution, attempts are made to keep the measured spot very small. However in known densitometers, which illuminate the measured spot with constant light intensity over the entire area, there are limits to the extent to which the spot can be reduced because the inaccuracy of measurement increases with resolution which arises because the result will be increasingly dependent on the position of the spot relative to the measured object. This applies particularly to the measurement of raster or pattern-like objects, e.g offset printing or the like, where even small changes in the position of the spot can result in considerable differences in the result.

The object of the invention, therefore, is to provide a measuring head of a densitometer so as to enable a smaller spot to be used and consequently higher resolution to be obtained with the same or even better accuracy or reliability of results.

As will be shown hereinafter this improvement is obtained by employing in accord with the invention a particular light intensity distribution over the spot area. There is disclosed a filter for providing the desired distribution which filter comprises a combination of lenses of transparent and neutral grey glass. British Patent Specification No. 982,520 discloses a non-refractive combination of a convex and concave lens, one of the two lenses being made of neutral-grey glass. The purpose of this combination of lenses is to compensate the known $Cos^4$ light loss in an objective, more particularly when used in TV systems. This publication does not disclose anything relating to the problem on which the present invention is based.

SUMMARY OF THE INVENTION

The present invention is based on the surprising discovery that if the intensity of the measuring light of the spot is reduced from the center of the spot to its periphery, the measurement becomes less sensitive to changes in relative position between the spot and the measured object, so that the spot can be reduced in size to improve resolution without affecting the accuracy.

The present invention is concerned with a measuring head in or for a densitometer and comprising a light source, a photoelectric transducer and an optical system for providing a light path between the source and the transducer via a location at which an object to measured is received, the optical system including means to form a defined spot of light at said location to illuminate an area of an object received thereat and means to guide light from the illuminated area to the transducer. The invention further provides means in said light path to provide at the transducer a light intensity response across the spot that follows a bell-shaped curve having its maximum at the center of the spot and being symmetrical about the spot center.

More particularly the aforementioned light intensity response may be obtained by the spot being given a light intensity distribution in accord with the bell-shaped curve to which end the said means in the light path is located in the portion of the path between the light source and the object location.

BRIEF DESCRIPTION OF THE DRAWINGS

The invention will now be described in greater detail with reference to the accompanying drawings, in which.

DESCRIPTION OF THE PREFERRED EMBODIMENT

Figure 1:
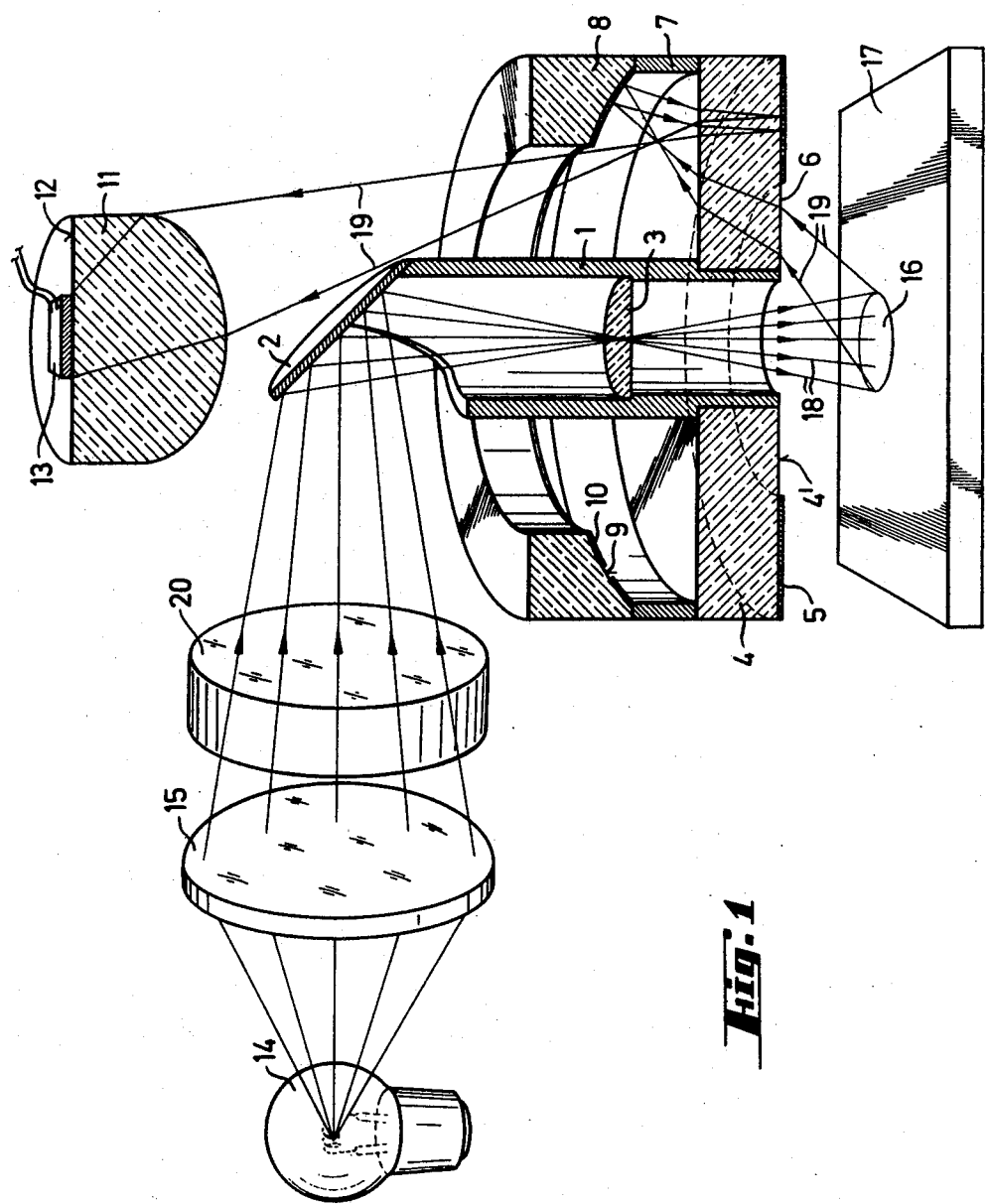
FIG. 1 shows, in perspective view, a longitudinal section through a densitometer measuring head according to the invention.

FIG. 1 shows only those more important parts of the densitometer measuring-head which are necessary for an understanding of the invention.

At the center of the entire optical system is a cylindrical focusing hood 1 open at both ends and having a plane reflecting mirror at its upper end as seen in the figure. The mirror is set at an angle with respect to the hood axis. A collecting lens 3 is disposed approximately at the middle of hood 1. At the bottom end of the hood there is an annular plane-parallel glass plate 4 having a vapour-deposited annular mirror 5 on its underside 4'. Mirror 5 does not cover the entire surface of plate 4 but leaves an inner annular gap 6 surrounding the hood and through which light can travel.

An annular glass member 8 is mounted on a spacer 7 above plate 4, i.e. in the direction towards mirror 2. Member 8 has a spherical concave annular surface 9 on its underside, on which a correspondingly spherical annular mirror 10 is vapour-deposited. An aplanatic lens 11 having a plane light exit pupil 12 is disposed above mirror 2 and a photoelectric transducer in the form of a silicon planar diode 13 is secured on lens 11.

Light from a source 14 travels via a lens 15 and a filter 20 (to be described hereinafter) and strikes mirror 2, is reflected thereby into hood 1, and concentrated by lens 3 to define a spot 16, e.g. about 1–3 mm in diameter, at a location at which an object being measured is located. The object is shown as having a surface 17 at which the defined spot of light is formed. The light rays from source 14 travel the first portion of the optical path terminating at the surface 17 where the rays 18 strike surface 17 at angles of 85°–90° in accordance with United States standard PH 2.17-1958. The second portion of the optical path lies between surface 17 and transducer 13 and as shown some rays 19 of the light reflected from the illuminated spot 16 on surface 17 travel through the gap 6, through plate 4, strike mirror 10 and are reflected by it back through plate 4 to the flat annular mirror 5. The light again travels through plate 4 through the annular space between hood 1 and member 8 and finally reaches the aplanatic lens 11, which directs it to photodiode 13. The geometry of the entire system is chosen so that light cannot reach the photodiode unless it is reflected at angles of 45°±5° to surface 17.

More details about the general mechanical and optical construction of the densitometer measuring head are to be found in Swiss Patent Specification No. 607,021 or the corresponding U.S. Pat. No. 4,078,858. The specific means by which there is obtained a weighted distribution on the light intensity across the spot in accord with this invention will now be further described.

Figure 2:
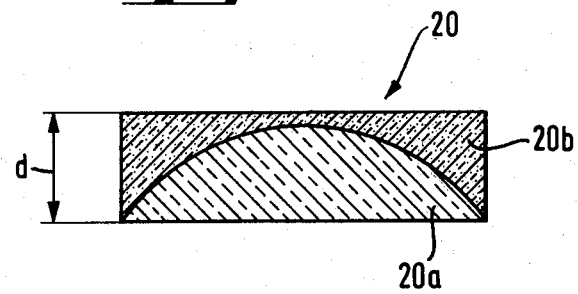
FIG. 2 is an axial section through the filter 20 shown in FIG. 1.

The filter 20 disposed in the first portion of the optical path of the measuring light is designed to provide a particular light intensity distribution across the spot 16 on surface 17. The filter is shown in axial section in FIG. 2 and comprises a plane-parallel plate made up of two lenses 20a and 20b. Lens 20a is plano-convex and fully transparent. Lens 20b is plano-concave and grey or black. Both lenses are made of glass having the same index of refraction, so that their combined optical effect on the paths of the light rays is like that of a homogeneous plane-parallel plate. The curved surfaces of both lenses are spherical and have a radius of curvature lying in the range of about 25 to 6 mm. In one embodiment, the radius of curvature was 12 mm. and the thickness of the plate was 1.2 mm. and its diameter was 10 mm., using NG 3 neutral grey glass for the element 20b.

Figure 3:
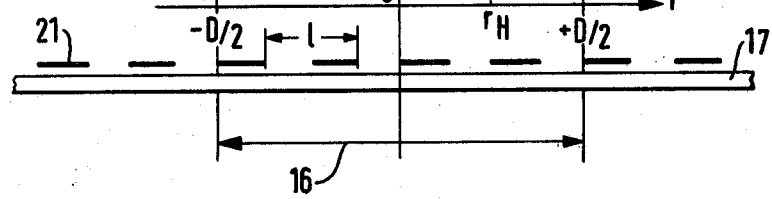
FIG. 3 is a diagram of the variation in intensity of the measured light across the spot, and FIG. 4 diagrammatically shows various measuring-error curves in dependence on the size of the spot.

Because the element 20b has an increasing axial thickness with increasing radius, the transmission of filter 20 thus decreases outwards from the optical axis. Consequently the intensity of light spot 16 decreases in accordance with a substantially bell-shaped curve outwards from the centre of the spot. This intensity curve is shown graphically in FIG. 3, where the ordinate shows the relative intensity I(r) relative to the maximum intensity $I_M$ at the center of spot 16 and the abscissa shows a distance r from the center of the spot. The spot diameter is D. FIG. 3 also shows an offset line pattern 21 at the surface 17 having a period l and the spot width 16. The bell-shaped curve is symmetrical about the spot center. The curve shown for one diametric plane is the same in all such planes.

The precise form of the intensity curve is of course closely dependent on the structure of filter 20. In practice it has been found advantageous if the intensity, I(r) substantially follows a bell-shaped curve, the intensity at the edge of the spot being 5–10% of the maximum value $I_M$ at the center of the spot. Outside the spot (where $r > D/2$) the intensity should be substantially zero. That distance $r_H$ from the center of the spot at which the intensity of the measured light has fallen by half, i.e. $Ir/I_M = 0.5$, should be between about 0.225 and 0.375 times the diameter D of the spot. This distance $r_H$ is known as the half-width. Preferably the distance $r_H$ is about 0.25 to 0.3 times the diameter D. The precise geometrical curve of intensity is unimportant. In order, however, to ensure adequate light intensity (strength of illumination) the bell curve should not be too narrow.

If the measuring filter 20 has the structure shown, the intensity curve may be closely approximated by the formula:

$$I(r) = I_M \cdot e^{-(\frac{r}{D})^2} \text{ for } -0.5D \leq r \leq +0.5D$$

In this formula, $\alpha$ is a constant which, in accordance with our previous remarks about the half-width, can be between 2.2 and 3.7. Preferably $\alpha$ is 2.8 and 3.4, more particularly between about 3.0 and 3.2.

FIG. 4 graphically shows the relative measuring error of a densitometer in dependence on the size of the spot for various intensity curves of the light spot striking the measured object. The root mean square error $\Delta X_{RMS}$ (the square root of the average sum of the squares of the errors over a number of measurements) is plotted along the ordinate. The abscissa gives the size $D/l$ of the spot relative to the offset raster period l.

Curve A is for the conventional method of illumination, in which the intensity of the measuring light is substantially constant across the entire spot. As can be seen, appreciable errors (over 2) occur when the diameter of the spot is relatively large. When the intensity is distributed according to the invention, however, the situation is considerably better. Curves B–D, which apply when the constant $\alpha = 2.8$, 3.0 and 3.2 in the preceding formula, clearly show that the measuring error in this case is below 1% even for a very small spot, measuring e.g. only two raster periods.

The densitometer measuring head particularly described above, for example, can be used to make a considerable reduction in the measuring error and also a considerable decrease in the measuring spot and consequent increase in resolution. The expense is very low, since the filter can be made very easily and economically from the two lenses.

The description hitherto has related only to reflection or incident-light densitometer. Of course, the intensity distribution across the spot according to the invention is also applicable to transmission or transmitted-light densitometers.

The filter 20 could alternatively be disposed in the second portion of the optical path between the surface 17 and the transducer 13, so as to weight the light intensity response of the transducer with respect to the spot in a manner that is equivalent to giving the spot the bell-shaped light intensity distribution that has been described.

What is claimed is:

1. In or for a densitometer, a measuring head comprising a light source, a photoelectric transducer and an optical system for providing a light path between the source and the transducer via a location at which an object to be measured is received, the optical system including means to form a defined spot of light at said location to illuminate an area of an object received thereat and means to guide light from the illuminated area to the transducer; the improvement comprising means in said light path to provide at the transducer a light intensity response across the spot that follows a bell-shaped curve having its maximum at the center of the spot and being symmetrical about the spot center.

2. A measuring head as claimed in claim 1 in which said means is located in the light path between said source and said object location to provide a light intensity distribution at said spot that is in accord with said bell-shaped curve.

3. A measuring head as claimed in claim 1 in which the intensity response is half the maximum value at the spot center at a distance from the spot center in the range of 0.2 to 0.4 times the defined spot diameter.

4. A measuring head as claimed in claim 1 in which the intensity response at the periphery of the defined spot is about 5 to 10% of the maximum value at the spot center.

5. A measuring head as claimed in claim 3 in which the intensity response at the periphery of the defined spot is about 5 to 10% of the maximum value at the spot center.

6. A measuring head as claimed in claim 1 in which the intensity response outside the defined spot is at least approximately zero.

7. A measuring head as claimed in claim 1 in which the intensity response is in accord with the formula:

$$I(r) = I_M \cdot \exp-(\alpha \cdot r/D)^2 \text{ for } -0.5D \leq r \leq +0.5D,$$

where
- $I(r)$ is the intensity at a radius r from the center of the spot;
- D is the diameter of the spot; and
- $\alpha$ is a constant in the range of 2.2 to 3.7.

8. A measuring head as claimed in claim 7 in which $\alpha$ is in the range of 2.8 to 3.4.

9. A measuring head as claimed in claim 8 in which $\alpha$ is in the range of 3.0 to 3.2.

10. A measuring head as claimed in claim 1 in which said means comprises a filter intersecting the optical axis of the light path and having a transmissivity which has a maximum on the optical axis and decreases symmetrically away from the axis.

11. A measuring head as claimed in claim 2 in which said means comprises a filter intersecting the optical axis of the light path and having a transmissivity which has a maximum on the optical axis and decreases away from the axis.

12. A measuring head as claimed in claim 10 in which said filter is a plane parallel plate comprising plano-convex and plano-concave lenses, the plano-concave lens being of lesser transparency than the plano-convex lens.

13. A measuring head as claimed in claim 11 in which said filter is a plane parallel plate comprising plano-convex and plano-concave lenses, the plano-concave lens being of lesser transparency than the plano-convex lens.

14. A measuring head as claimed in claim 12 in which said plano-concave lens is of a neutral grey glass.

15. A measuring head as claimed in claim 13 in which said plano-concave lens is of a neutral grey glass.

16. A measuring head as claimed in claim 12 in which the curved surfaces of said lenses are spherical surfaces.

17. A measuring head as claimed in claim 13 in which the curved surfaces of said lenses are spherical surfaces.

18. A measuring head as claimed in claim 2 in which said means comprises a parallel plate optical member constituted by plano-concave and plano-convex lenses having the same index of refraction and mating curved surfaces and the plano-concave lens being made of a neutral grey glass.

19. A measuring head as claimed in claim 18 in which the curved surfaces are spherical surfaces.

* * * * *

UNITED STATES PATENT AND TRADEMARK OFFICE
CERTIFICATE OF CORRECTION

PATENT NO. : 4,341,473
DATED : July 27, 1982
INVENTOR(S) : Fred Mast

It is certified that error appears in the above—identified patent and that said Letters Patent is hereby corrected as shown below:

Column 4, line 14, change "(over 2)" to --(over 2%)--

Signed and Sealed this

Fifth Day of October 1982

[SEAL]

Attest:

GERALD J. MOSSINGHOFF

Attesting Officer     Commissioner of Patents and Trademarks